United States Patent [19]

Whyte

[11] 4,094,312

[45] June 13, 1978

[54] WALKING BOOT FOR SURGICAL LEG CAST

[76] Inventor: Francis Whyte, 2 Cascade Dr., Halifax, Nova Scotia, Canada

[21] Appl. No.: 749,916

[22] Filed: Dec. 13, 1976

[51] Int. Cl.$^2$ ............................................. A61F 5/04
[52] U.S. Cl. .................................................. 128/83.5
[58] Field of Search ........................... 128/83.5, 83, 82

[56] References Cited

U.S. PATENT DOCUMENTS

| | | | |
|---|---|---|---|
| 3,800,376 | 4/1974 | Whyte | 128/83.5 |
| 3,802,424 | 4/1974 | Newell | 128/83.5 X |

Primary Examiner—John D. Yasko

[57] ABSTRACT

A boot, for use with a surgical plaster of Paris leg cast, comprising a shoe and an upper. The shoe is of rigid sheet material with a pair of wells of similar depth located in the sole and heel portions. The upper is flexible to receive the foot of the cast and the lower periphery of the upper is inturned and fixed at least to the outer periphery of the shoe. In one embodiment the inturned lower periphery of the upper forms a bottom with apertures to receive the wells of the shoe.

11 Claims, 4 Drawing Figures

WALKING BOOT FOR SURGICAL LEG CAST

This invention relates to a boot for use with a surgical plaster of Paris leg cast.

To overcome, at least partially, the problems associated with a surgical plaster of Paris leg cast the present inventor has previously developed a shoe for use with such a cast, is disclosed in U.S. Pat. No. 3,800,376 issued Apr. 2, 1974. However, to use such a shoe it is necessary to tape the shoe to the cast, which is inconvenient.

It is an object of the present invention to provide a boot which has a sole and heel giving support to the cast and which may be placed on the cast without taping.

In its broadest aspect the invention consists of a boot, for use with a surgical plaster of Paris leg cast, comprising: a shoe formed of a sheet member of substantially rigid, weight supporting material having an outline substantially similar to the profile of the underside of a foot, a pair of wells of similar depth formed in the sheet member, one well being located in the forward portion of the sheet member and of an area substantially covering the weight bearing area of the sole portion of the foot, the other well being located in the rearward portion of the sheet member and of an area substantially covering the weight bearing area of the heel portion of the foot, the edge portion of the sheet material forming a peripheral flange; and a flexible upper constructed and arranged to receive the foot portion of the cast, the lower periphery of the upper being inturned and fixed at least to the peripheral flange of the shoe. In an alternate embodiment the lower inturned periphery of the upper may form a bottom with apertures to receive the wells of the shoe whereby the shoe rests on the bottom, either loosely or fixed thereto, and the wells project downwardly through the apertures.

The cast having the shoe of applicant's above-mentioned United States patent attached to it may be exposed to adverse weather and ground conditions when used. In other words, rain and mud may cause the cast to deteriorate or at least soil it and the projecting toes of the foot.

It is a further object of the invention to provide a boot for use with a surgical plaster of Paris leg cast having a shoe fixed to its underside.

In another aspect the invention consists of a boot for use with a surgical plaster of Paris leg cast having a shoe fixed thereon, the shoe comprising a sheet member of substantially rigid weight supporting material having a pair of wells formed therein, one well underlying the sole portion of the foot and another well underlying the heel portion of the foot, the shoe being held to the cast by a plurality of turns of bandage encircling the foot portion of the leg cast and the shoe at least between said wells; the boot comprising an upper and a bottom, the upper being flexible and constructed and arranged to receive the foot portion of the cast, the bottom having a pair of apertures therein to receive the wells of the shoe whereby the wells project through the apertures.

Example embodiments of the invention are shown in the accompanying drawings in which.

Figure 3:
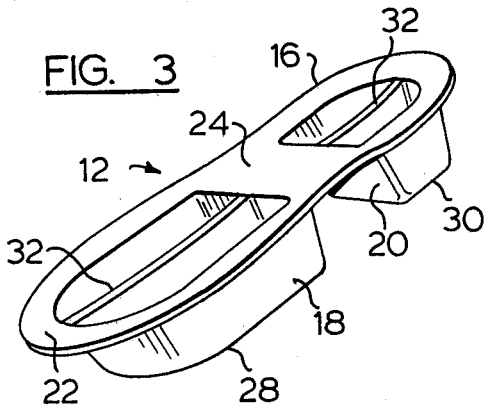

FIG. 3 is a perspective view of a shoe of prior U.S. Pat. No. 3,800,376; and

Figure 4:
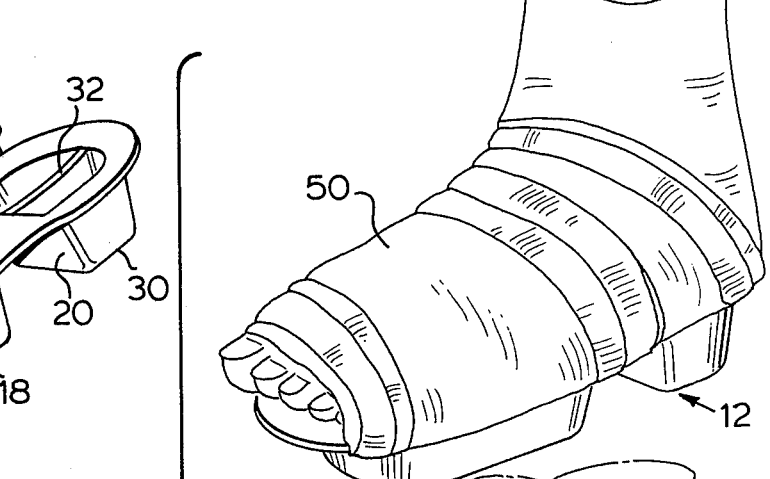
Figure 4:
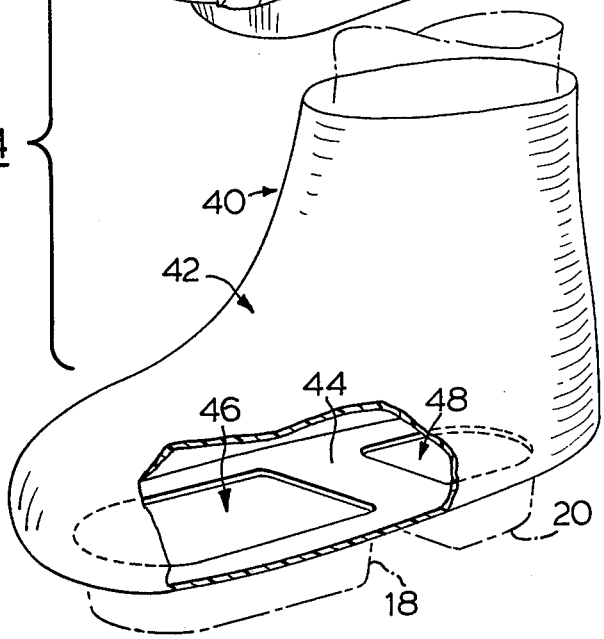

FIG. 4 is a perspective view, partly cut away, of a second embodiment of the boot of the invention showing a cast, carrying the shoe of FIG. 3, receivable in the boot.

Figure 1:
FIG. 1 is a perspective view, partly cut away, of a boot having a sole and heel portion fixed to an upper portion.
Figure 2:
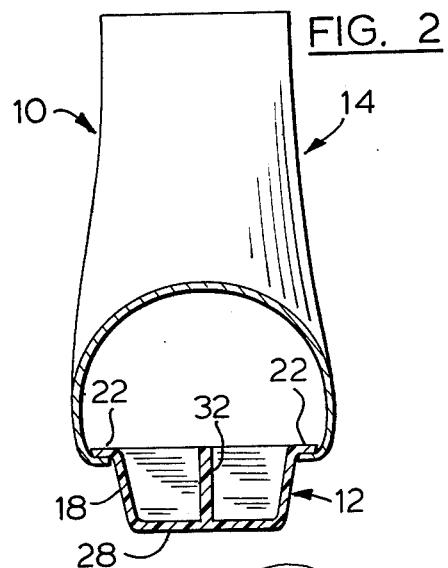
FIG. 2 is a cross-sectional view taken along line 2—2 of FIG. 1.

The embodiment shown in FIGS. 1 and 2 of the drawings consist of a boot 10 having a shoe 12 and an upper 14. Shoe 12 is substantially of the same construction and configuration as the shoe shown in FIG. 3, which is the subject matter of the above-mentioned prior patent, and comprises a sheet member 16 of substantially rigid, weight supporting material having an outline substantially similar to the profile of the underside of a foot. Two wells of similar depth are formed in sheet member 16, one well 18 in the forward portion of the sheet member and substantially covering the weight bearing area of the sole of the foot, and the other well 20 in the rearward portion of the sheet member and substantially covering the weight bearing area of the heel of the foot. The edge portion of sheet member 16 between wells 18 and 20 and the edge of the sheet member forms a peripheral flange 22. Between wells 18 and 20 sheet member 16 forms a bridge 24 which is preferably contoured to form a raised portion in the area of the instep of the foot. The bottom portion 28 of well 18 is preferably flattened to provide a weight bearing area and the bottom portion 30 of well 20 is preferably rounded. Sheet member 12 is substantially rigid and of sufficient thickness to carry the weight to be borne through the cast, but the sheet member also has some flexibility, a suitable material for the purpose being ABS (acryloritrile butadiene styrene).

Preferably wells 18 and 20 may be suitably sectioned by one or more fixed vertical divider walls 32, the upper edge of the divider wall being below the plane of the upper surface of flange 22.

Upper 14 of boot 10 consists of flexible sheet material formed with a flat bottom 36 having a pair of apertures 38 through which wells 18 and 20 project. Flange 22 and bridge 24 lie against bottom 36 and may be fixed to the bottom by suitable means such as adhesive. It may be preferred to fabricate boot 10 by omitting bottom 36 and inturning the lower edge of upper 14 to form a circumferential flange adhering to flange 22 of shoe 12. Of course upper 14 is shaped to receive a surgical plaster of Paris leg cast.

The embodiment shown in FIG. 4 of the drawings consists of a boot 40 having an upper 42 with a flat bottom 44. A pair of apertures 46 and 48 are located in bottom 44 of a size to receive wells 18 and 20 of a shoe 12 which is shown per se in FIG. 3 and shown in FIG. 4 attached to a surgical plaster of Paris leg cast 50. As before, upper 42 is shaped to receive cast 50 with shoe 12 attached to the cast whereby wells 18 and 20 are inserted through apertures 46 and 48 in the manner shown in broken lines in FIG. 4.

I claim:

1. A boot, for use with a surgical plaster of Paris leg cast, comprising:

a shoe formed of a sheet member of substantially rigid, weight supporting material having an outline substantially similar to the profile of the underside of a foot, a pair of wells of similar depth formed in the sheet member, one well being located in the forward portion of the sheet member and of an area substantially covering the weight bearing area of the sole portion of the foot, the other well being located in the rearward portion of the sheet member and of an area substantially covering the weight bearing area of the heel portion of the foot, the edge portion of the sheet material forming a peripheral flange; and a flexible upper constructed and arranged to receive therein the foot portion of the cast, the lower periphery of the upper being inturned to form a bottom having apertures therein to receive the wells of the shoe whereby the wells project downwardly through the apertures.

2. A boot as claimed in claim 1 in which the bottom is fixed to the shoe.

3. A boot as claimed in claim 1 in which that portion of the sheet member forming a bridge between the walls is contoured to provide a raised instep.

4. A boot as claimed in claim 1 in which the material of the sheet member is acrylonitrile butadiene styrene.

5. A boot as claimed in claim 1 in which the sheet member is coated with rubber.

6. A boot as claimed in claim 1 in which at least the forward well is flattened in its bottom portion.

7. A boot as claimed in claim 1 in which the upper is waterproof.

8. A boot as claimed in claim 1 in which at least one of the wells includes a fixed, vertical divider wall therein.

9. A boot for use with a surgical plaster of Paris leg cast having a shoe fixed thereon, the shoe comprising a sheet member of substantially rigid weight supporting material having a pair of wells formed therein, one well underlying the sole portion of the foot and another well underlying the heel portion of the foot, the shoe adapted to be held to the cast by a plurality of turns of bandages encircling the foot portion of the leg cast and the shoe at least between said wells, the boot comprising an upper and a bottom, the upper being flexible and constructed and arranged to receive the foot portion of the cast, the bottom having a pair of apertures therein to receive the wells of the shoe whereby the wells project downwardly through the apertures.

10. A boot as claimed in claim 9 in which the material of the upper is waterproof.

11. A boot as claimed in claim 9 in which the material of the upper is rubber.

* * * * *